United States Patent [19]

Foslien

[11] Patent Number: 4,478,362

[45] Date of Patent: Oct. 23, 1984

[54] STAPLER CARTRIDGE WITH ANGULARLY DISPOSED STAPLE GUIDE TRACK PORTIONS

[75] Inventor: Floyd L. Foslien, Stillwater, Minn.

[73] Assignee: Minnesota Mining and Manufacturing Company, Saint Paul, Minn.

[21] Appl. No.: 147,480

[22] Filed: May 7, 1980

[51] Int. Cl.³ .......................... B25C 5/08; B25C 5/11; A61B 17/04

[52] U.S. Cl. ..................................... 227/19; 227/120; 227/DIG. 1

[58] Field of Search ................. 227/19, 107, 119, 120, 227/139, 145, 147, DIG. 1; 128/334 R

[56] References Cited

U.S. PATENT DOCUMENTS

| | | | |
|---|---|---|---|
| 1,041,884 | 10/1912 | Sasseman | 227/119 |
| 1,923,377 | 8/1933 | Hughes | 227/139 |
| 2,090,831 | 8/1937 | Burkhardt . | |
| 2,577,012 | 12/1951 | Hinckley et al. . | |
| 2,966,681 | 1/1961 | Campbell . | |
| 3,022,509 | 2/1962 | De Man | 227/147 X |
| 3,581,350 | 6/1971 | McComb | 227/120 X |
| 3,672,555 | 6/1972 | Korth | 227/120 |
| 4,033,499 | 7/1977 | Butler | 227/120 |
| 4,202,480 | 5/1980 | Annett | 227/19 X |
| 4,256,251 | 3/1981 | Moshofsky | 227/120 |

FOREIGN PATENT DOCUMENTS 1957334 5/1981 Fed. Rep. of Germany ...... 227/120

Primary Examiner—Paul A. Bell
Attorney, Agent, or Firm—Donald M. Sell; William L. Huebsch

[57] ABSTRACT

A cartridge which dispenses staples into a stapler from a track that has track portions which are not linearly aligned so that the cartridge can be shaped for minimum interference with the use of the stapler.

15 Claims, 10 Drawing Figures

STAPLER CARTRIDGE WITH ANGULARLY DISPOSED STAPLE GUIDE TRACK PORTIONS

BACKGROUND OF THE INVENTION

This application relates to cartridges for staplers, and in one important aspect to cartridges for staplers of the type used in the medical field to join disunited tissues.

The art is replete with staplers having cartridges from which staples are fed seriatim into the mechanisms of the staplers. Typically such a stapler includes a housing having a passageway with an outlet opening, and having an inlet opening through which the cartridge feeds staples into the passageway. A ram is mounted on the housing for sliding movement between a load position with the ram spaced from the inlet opening to allow the cartridge to feed a staple into the passageway, and an eject position at which the ram pushes the staple out of the outlet opening so that the staple will engage the structure to be stapled, and may be clenched either against an anvil positioned on the opposite side of the structure or around an anvil projecting across the end of the passageway.

Such a stapler adapted for use in the medical field is described in U.S. Pat. No. 4,202,480. The stapler described in that application is of the type having an anvil projecting across the end of the passageway, and is activated by manually squeezing together toggle linkages on opposite sides of the path for the ram to move the ram to its eject position so that it will clench the staple around the anvil. The cartridge for supplying staples to the inlet opening projects generally at right angles to the direction of travel of the ram close to the outlet opening for the passageway and thus can obstruct vision of a person using the stapler to join disunited tissues, particularly if the cartridge is designed to contain a large number of staples.

SUMMARY OF THE INVENTION

The present invention affords storing staples along non-linear tracks in cartridges so that cartridges can be both adapted to contain a large numbers of staples and given a shape that will not interfere with the effective use of the stapler.

According to the present invention there is provided a stapler cartridge comprising a plurality of conventional generally U-shaped staples each having a central portion and a leg projecting from each end of the central portion. Means are provided for defining a track for guiding the staples comprising guide surfaces spaced to guide opposite sides of the central portions of the staples along the track and to restrict relative displacement of the central portions of the staple transverse of the track. The track comprises portions disposed with respect to each other at an included angle of less than 180 degrees, with the staples being disposed along the track with their legs projecting away from the side of the track opposite the included angle, and means are provided for biasing the central portions of the staples along the track toward a first end thereof through which staples can exit the cartridge.

The portions of the track can be intersecting linear portions so long as the portions intersect at an included angle that is greater than about 90 degrees, or the track can include an arcuate part which allows the track to have portions disposed at an angle with respect to each other of less than 90 degrees. In either case pressure against the central portions of staples to move them along the track will bias the staples to a position with their legs projecting generally at right angles to the track, (i.e. radially outwardly of the axis of the track in the case of an arcuate part of the track) where the staples occupy a shorter portion of the track than they would if their legs were disposed at less than a ninety degree angle with respect to the track. This biasing of the staples will occur provided the guide surfaces will not allow the central portions of the staples to be substantially displaced transverse of the track (e.g. 0.003 inch clearance for a 0.022 inch thick staple); and allows the staples to move along linear portions of the track, through intersections between intersecting linear portions of the track, and around arcuate portions of the track as pressure is applied against the central portion of the staples to feed them into a stapler.

A cartridge according to the present invention has advantages when used with stapler mechanisms of the type described above in that the cartridge can have a long linear track portion extending parallel to the ram for the stapler and in which the staples are positioned side by side with their legs projecting away from the ram to provide a high capacity cartridge with a profile that will not project sufficiently from the rest of the stapler to interfere with the vision of a person using the stapler; which linear track is connected to the inlet opening to the passageway for the ram by a portion of the track including an arcuate part that causes the staples to pivot 90 degrees so that their legs point toward the outlet end of the passageway before they are fed into its inlet opening. Additionally, the portion of the track adjacent the inlet opening to the passageway can be disposed at an acute angle (e.g., 75 degrees) with respect to the portion of the passageway between its inlet and outlet openings, so that the pressure applied to the central portion of the staples to move them along the track which biases their legs to a position projecting at right angles to the track will cause the distal ends of the legs of the staple at the inlet opening to be biased against a staple guide surface opposite the inlet opening and aligned with the passageway for the ram so that the staple will be aligned with the ram and the possibility of the legs catching on the stapler housing around the inlet opening will be minimized.

BRIEF DESCRIPTION OF THE DRAWING

The present invention will be more thoroughly explained with reference to the accompanying drawing where like numbers refer to like parts in several views, and wherein.

DESCRIPTION OF THE PREFERRED EMBODIMENT

Figure 1:
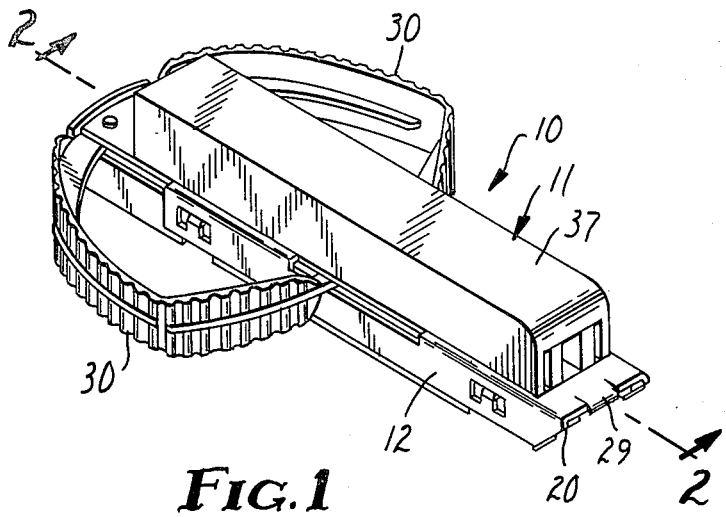
FIG. 1 is a perspective view of a stapler incorporating a first embodiment of a stapler cartridge according to the present invention.
Figure 2:
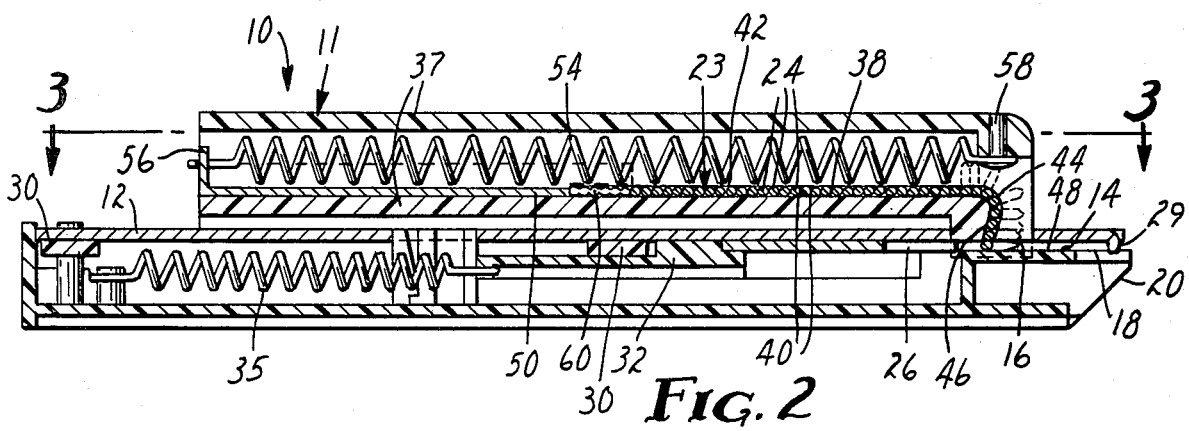
FIG. 2 is an enlarged sectional view taken approximately along lines 2—2 of FIG. 1.
Figure 3:
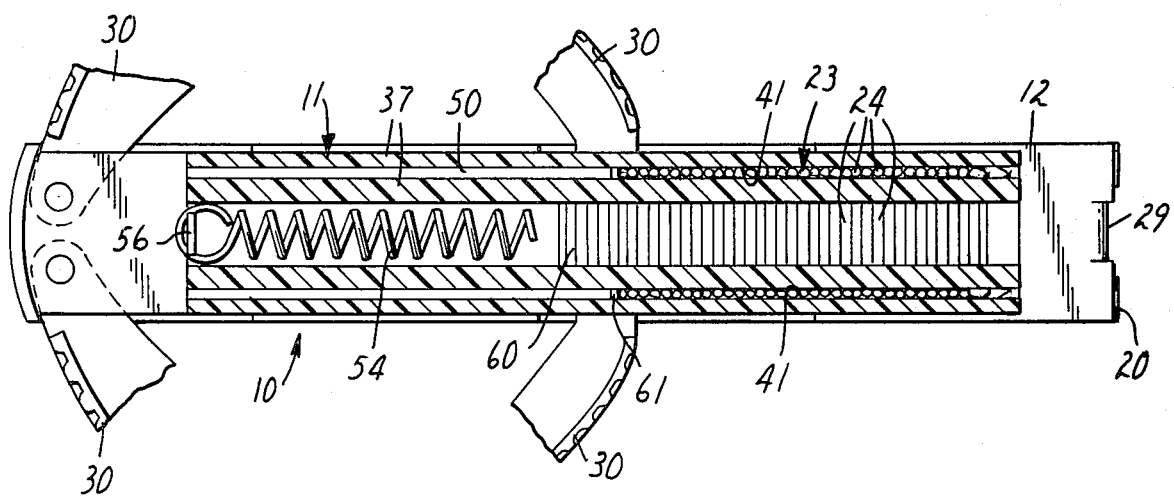
FIG. 3 is a fragmentary sectional view taken approximately along lines 3—3 of FIG. 2.
Figure 4:
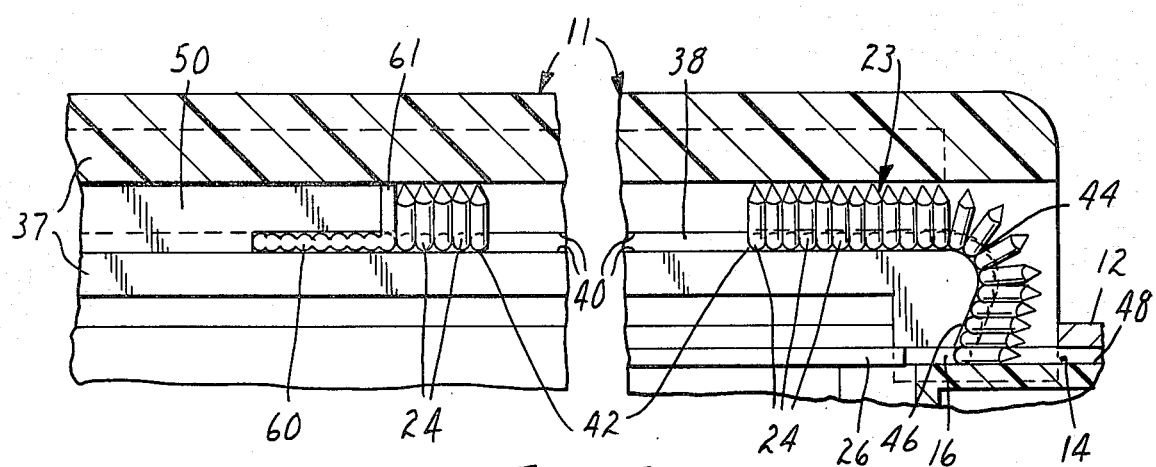
FIG. 4 is an enlarged fragmentary sectional view taken approximately along lines 2—2 of FIG. 1.

Referring now to FIGS. 1 through 6 of the drawing, there is shown a first embodiment of a stapler generally designated by the number 10 which includes a cartridge or magazine 11 according to the present invention.

Except for the substitution of the novel cartridge 11, the stapler 10 has generally the same structure as that of the stapler disclosed in U.S. Pat. No. 4,202,480, the disclosure whereof is incorporated herein by reference.

Briefly the stapler 10 comprises a housing 12 having a passageway 14 (FIG. 2) extending from an inlet opening 16 to an outlet opening 18 at an end 20 of the housing 12, which passageway 14 is adapted to guide a single staple 24 moved from the inlet opening 16 to the outlet opening 18. The cartridge 11 provides means for biasing a stack or row 23 of the staples 24 into the inlet opening 16. A ram 26 is mounted on the housing 12 for sliding movement from a load position (FIG. 2) with the ram 26 spaced from the inlet opening 16 to afford movement of one of the staples 24 into the passageway 14, along the passageway 14 with an end portion of the ram 26 pushing the staple 24 to an eject position at which the ram 26 pushes the staple 24 out the outlet opening 18 and forms the staple 24 around an anvil portion 29 of the housing 12 projecting across the outlet opening 18. The stapler 10 illustrated is particularly adapted for use by surgeons to join disunited skin into which the ends of the staples 24 formed around the anvil portion 29 are clenched, after which the anvil portion 29 is retracted from the central portion of the clenched staple 24; which type of stapling is well known in the art.

Drive means manually activatable by manually pressing opposed flexible handle members 30 together is provided for propelling a drive member 32 along the passageway 14 to move the ram 26 from its load to its eject position, whereupon the resiliently flexible nature of the handle members 30 and a coil spring 35 will cause the drive member 32 to return to its initial position and means (not shown) for coupling the drive member 32 to the ram 26 after the handle members 30 have been pressed together sufficiently to move the ram 26 to its eject position will return the ram 26 to its load position.

The stapler cartridge 11 includes a housing 37 containing a plurality of the generally U-shaped staples 24, each of which has a central portion and a leg projecting from each end of its central portion. The cartridge housing 37 has walls with surfaces that provide means for defining a track 38 along which the staples 24 are positioned, which track 38 has a first end opening into the inlet opening 16 of the stapler 10, which surfaces include opposed guide surfaces 40 (FIG. 2) spaced to guide opposite sides of the central portion of the staples 24 along the track 38 and restrict relative displacement of the central portions of the staples 24 transverse of the track 38 in a direction at right angles to the axis of the central portion; and parallel leg guide surfaces 41 (FIG. 3), which leg guide surfaces 41 are closely spaced from the outer surfaces of the legs of staples along the track 38 to restrict movement of the staples 24 transverse of the track 38 in a direction parallel with the central portions of the staples, while allowing the legs of the staples 24 to pivot around their central portions. The housing walls define various portions of the track 38 including a long linear portion 42 extending parallel to the direction of movement of the ram 26; a portion adjacent the long linear portion 42 that is arcuate and extends for over ninety degrees about an axis parallel to the opposed guide surfaces 40, and a short linear portion 46 between the arcuate portion 44 and the inlet opening 16 to the passageway 14.

The staples 24 are maintained along the linear portion 42 of the track 38 with their legs projecting away from the ram 26 generally at right angles to the track 38 and along the arcuate portion 44 with their legs projecting generally away from the axis of the arcuate portion 44 by means for biasing the central portions of the staples along the track 38 toward the inlet opening 16. The short linear portion 46 between the arcuate portion 44 and the inlet opening is disposed at an acute angle of slightly less than ninety degrees (i.e. 75 to 79 degrees) with respect to the portion of the passageway 14 between the inlet opening 16 and the outlet opening 18 (toward which outlet opening 18 the legs of the staples 24 project) so that the forces which tend to cause the legs of the staples 24 to project at right angles to the short linear portion 46 of the track 38 will bias the legs of the staple in the inlet opening 16 against a staple guide surface 48 on the housing opposite the inlet opening 16 to ensure that that the staple is properly aligned with the passageway 14 when it is engaged by the ram 26.

Figure 5:
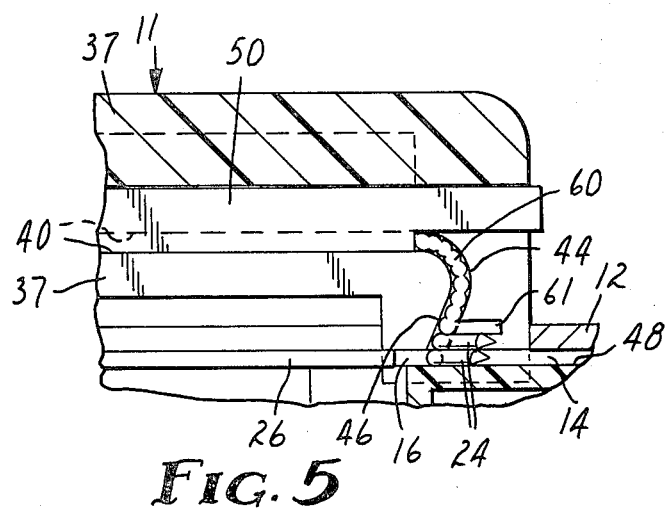
FIG. 5 is an enlarged fragmentary sectional view taken approximately along the lines 2—2 of FIG. 1, but showing a flexible follower plate incorporated in the cartridge pressing the last two staples in the cartridge into the stapler.
Figure 6:
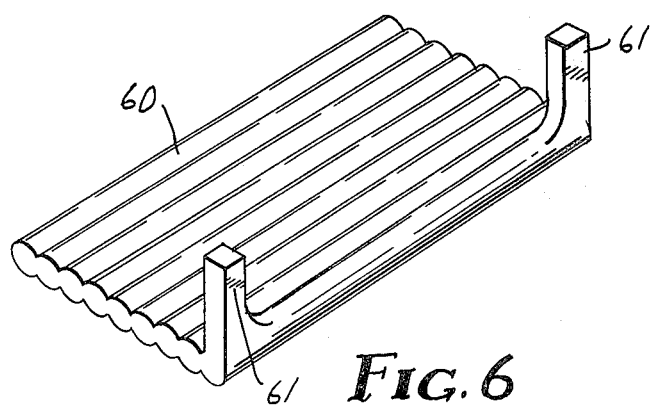
FIG. 6 is an enlarged sectional view of the flexible follower plate.
Figure 7:
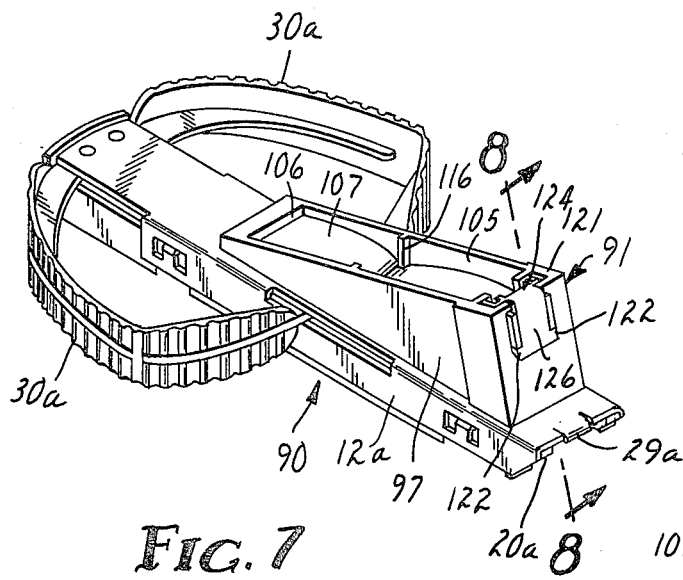
FIG. 7 is a perspective view of a stapler incorporating a second embodiment of a stapler cartridge according to the present invention.
Figure 10:
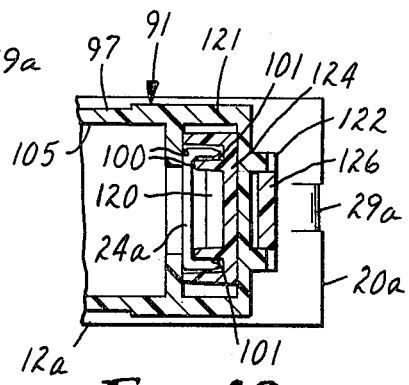
FIG. 10 is a fragmentary sectional view taken approximately along lines 10—10 of FIG. 8.

The means for biasing the central portions of the staples along the track 38 toward the inlet opening 16 comprises a follower 50 including a generally U-shaped portion adapted to slide along the long linear portion 42 of the track 38, and a coil spring 54 tensioned between a tab 56 on the follower 50 and a pin 58 in the cartridge housing 37 to bias the follower 50 along the track 38 toward its first end. A flexible follower plate 60 having a width and thickness approximately equal to that of the central portions of the staples 24 and a length slightly longer than the arcuate and short linear portions 44 and 46 of the track is disposed between the follower 50 and the adjacent staple 24 in the track 38. The flexible follower plate 60 is of a flexible material (e.g, polypropylene) and is transversely grooved to allow it to bend and follow around the arcuate portion 44 and along the short linear portion 46 of the track so that it will press the last of the staples into the inlet opening 16 (FIG. 5). The follower plate 60 has ears 61 projecting at generally a right angle from its end adjacent the staples 24 which ears 61 engage the legs of the adjacent or last staple 24 in the cartridge 11 to ensure that that last staple 24 will enter the inlet opening 16 at the proper attitude. Without the flexible follower plate 60 a certain number of staples could not be dispensed from the cartridge 11, which, depending on the relative cost between staples 24 and the flexible follower plate 60, may be an economically acceptable alternative; however, such use of staples instead of the follower plate 60 may be undesirable due to the possible appearance to a user of wastefulness or that the stapler has malfunctioned before all of the staples have been dispensed from the cartridge 11.

Referring now to FIGS. 7 through 10 of the drawing, there is shown a stapler generally designated by the number 90 which includes a second embodiment of a cartridge or magazine 91 according to the present invention.

Except for the substitution of the novel cartridge 91, the stapler 90 has generally the same structure as that of the stapler disclosed in U.S. Pat. No. 14,911, and the stapler 10 described above so that similar parts of the stapler 90 will be referred to by the same reference numerals used to refer to parts of the staples 10 except for the addition of the suffex "a".

Briefly, like the stapler 10, the stapler 90 is a skin stapler comprising a housing 12a having a passageway 14a(FIGS. 8 and 9) extending from an inlet opening 16a to an outlet opening 18a at an end 20a of the housing 12a, which passageway 14a is adapted to guide a single staple 24a moved from the inlet opening 16a to the outlet opening 18a. The cartridge 91 provides means for biasing a row or stack 93 of the staples 24a into the inlet opening 16a. A ram 26a is mounted on the housing 12a for sliding movement from a load position (FIG. 8) with the ram 26a spaced from the inlet opening 16a to afford movement of one of the staples 24a into the passageway 14a along the passageway 14a with an end portion of the ram 26a pushing the staple 24a to an eject position at which the ram 26a pushes the staple 24a out the outlet opening 18a and forms the staple around an anvil portion 29a of the housing 12a projecting across the outlet opening 18a.

Drive means manually activatable by manually pressing opposed flexible handle members 30a together is provided for propelling a drive member (not shown) along the passageway 14a to move the ram 26a from its load to its eject position, whereupon the resiliently flexible nature of the handle members 30a and a coil spring (not shown) will cause the drive member to return to its initial position and means (not shown) for coupling the drive member to the ram 26a after the handle members 30a have been pressed together sufficiently to move the ram 26a to its eject position will return the ram 26a to its load position.

The stapler cartridge 91 includes a two part housing 97 containing a plurality of the generally U-shaped staples 24a, each of which staples 24a has a central portion and a leg projecting from each end of its central portion. The cartridge housing 97 has walls with surfaces that provide means for defining a track 98 along which the staples are positioned, which track 98 has a first end opening into the inlet opening 16a of the stapler 90, which surfaces include opposed quide surfaces 100 (FIGS. 8 and 9) spaced to guide opposite sides of the central portion of the staples 24a along the track 98 and restrict relative displacement of the central portions of the staples 24a transverse of the track 98 in a direction at right angles to the axis of the central portion; and parallel leg guide surfaces 101 (FIG. 10) which intersect and extend away from the guide surface 100 adjacent the end 20a of the stapler housing 12a, which leg guide surfaces 101 are closely spaced from the inner surfaces of the legs of staples 24a along the track 98 to restrict movement of the staples 24a transverses of the track 98 in a direction parallel with the central portions of the staples, while allowing the legs of the staples 24a to pivot around their central portions. The walls of the cartridge housing 97 define various portions of the track 98 including a long linear portion 102 which is disposed at more than a 90 degree angle with respect to the portion of the passageway 14a between the inlet opening 16a and and outlet opening 18a to decrease the distance that the cartridge projects from the housing 12a; and a short linear portion 104 which intersects the long linear portion 102 at an included angle of about 153 degrees extends between the long linear portion 102 and the inlet opening 16a, and is displaced at an acute angle with respect to the portion of the passageway 14a between the inlet opening 16a and the outlet opening 18a to help bias the legs of the staples 24a into the inlet opening 16a and against a staple guide surface 48a as will later be explained.

Figure 9:
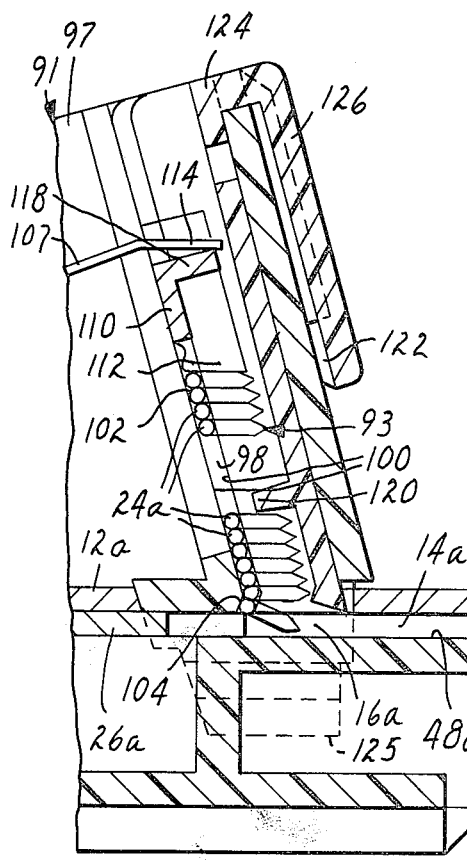
FIGS. 8 and 9 are enlarged fragmentary sectional view taken approximately along lines 8—8 of FIG. 7 which show two positions of a ram in the stapler and the corresponding positions of stamples being fed into a passageway for engagement by the ram.
Figure 8:
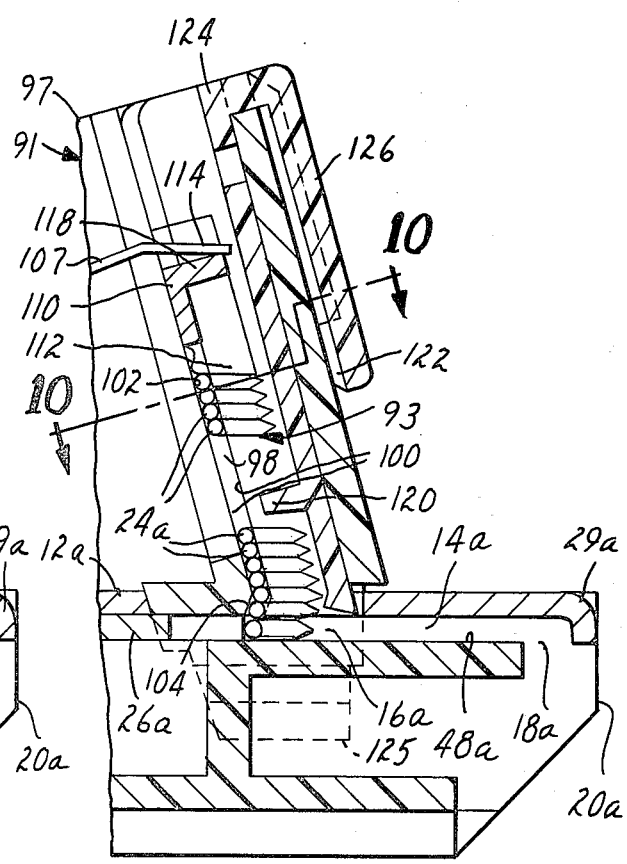

The staples 24a are positioned along the track 98 with their legs projecting away from the side of the track 98 opposite the included angle between the intersecting track portions 102 and 104 and generally toward the end 20a of the staple 90, and are biased toward a position with their legs projecting at right angles to the track 98 by means including a spring 107 and a follower 110 for biasing the central portions of the staples 24a along the track 98 toward the inlet opening 16a. Because of the acute angle of slightly less than ninety degrees (i.e., 75 to 79 degrees) at which the short linear portion 104 of the track 98 is disposed with respect to the portion of the passageway 14a between the inlet opening 16a and the outlet opening 18a, the legs of the staple at the inlet opening 16a will be biased against the staple guide surface 48a on the housing 12a opposite the inlet opening 16a as the ram 26a uncovers that opening 16a during movement from its eject position back to its load position (FIG. 9). This ensures that the staple will properly enter the inlet opening 16a and is subsequently aligned with the passageway 14a (FIG. 8) for engagement by the ram 26a.

The generally U-shaped follower 110 included in the means for biasing the central portions of the staples along the track 98 toward the inlet opening 16a has legs adapted to slide along the long linear portion 102 of the track 98. The flat spring 107 is received in a cavity 105 in the cartridge housing 97 with one end portion 106 of the spring 107 supported on the cartridge housing 97 and a central portion of the spring 107 restrained below opposed triangular projections 116 extending into the cavity 105 so that a narrow end portion 114 of the spring 107 opposite the end portion 106 will bias the follower 110 against the stack of staples 24a along the track 98 toward the inlet opening 16a. The legs of the follower 110 have ends 112 which project sufficiently toward the inlet opening 16a to press the last staple 24a in the cartridge 91 along the short portion 104 of the track into the inlet opening 16a while the central portion of the follower 110 is still along the long portion 102 of the track. The ends 112 of the follower 110, however, cannot enter the inlet opening 16a due to engagement of ledges 118 and 120 on the follower 110 and the cartridge housing 97 respectively, which engagement stops movement of the follower 110 under the influence of the spring 107.

The two parts of the cartridge housing 97 comprise a case part 121 having hook-like projections 125 adapted to releasably engage the housing 12a, and a guide part 124 releasably retained in a channel defined by retangular walls of the case portion 120 via a T-shaped tab 126 releasably engaged under spaced projections 122 on the outer wall of the case part 121. The guide part 124 has spaced flanges which with the adjacent walls of the case part 121 define the track 38a for the stack of staples 24a in the cartridge 91.

While the two embodiments 11 and 91 of a stapler cartridge according to the present invention are exemplary of cartridges that can be designed utilizing the underlying principals of the present invention, many other cartridge shapes tailored to specific staplers could be made using those principals. Thus the scope of the present invention should not be limited by the structure of the cartridges and cartridge-stapler combination described, but should only be limited by the recitations in the claims and their equivalents.

I claim:

1. A stapler cartridge comprising:

a plurality of generally U-shaped staples each having a central portion and a leg projecting from each end of said central portion;

means for defining a track having an end and comprising surfaces spaced to guide opposite sides of the central portion of said staples along said track and restrict relative displacement of the central portions of said staples transverse of said track, said track comprising portions disposed with respect to each other at an included angle of less than 180 degrees and an arcuate portion between said portions which is arcuate about an axis parallel to said surfaces, and having said staples disposed along its length with their legs projecting generally normally away from said track on the side opposite said included angle with the staples along said arcuate portion being disposed with their legs projecting generally normally away from the axis of said arcuate portion; and means for biasing the central portions of said staples along said track toward said end comprising a flexible follower plate having a width and thickness similar to the width and thickness of the central portions of said staples, having one end in contact with one of said staples and being flexible about an axis transverse of its width to allow it to move around said arcuate portion to press said staples toward said end.

2. A stapler cartridge according to claim 1 wherein said track portions are adjacent and are both linear.

3. A stapler comprising:

a housing having a passageway with an inlet opening and an outlet opening;

a plurality of generally U-shaped staples each having a central portion and a leg projecting from each end of said central portion;

staple support means affixed to said housing and defining a track for said staples having a first end communicating with said inlet opening, said staple support means comprising surfaces spaced to guide opposite sides of the central portions of said staples along said track and to restrict relative displacement of the central portions of said staples transverse of said track, said track comprising a first portion adjacent said first end, which first portion is disposed at an acute included angle with respect to a portion of said passageway between said inlet and outlet openings, and said staples along said first portion of said track being disposed with the distal ends of their legs directed generally toward said outlet opening;

means for biasing the central portions of said staples along said track toward said inlet opening so that the distal ends of the legs of the staple at said inlet opening will be biased toward a position at a right angle to said first portion and thereby into said passageway;

a ram having an end portion adapted to engage one of the staples and being mounted on said housing for sliding movement in a first linear direction between a load position with the ram spaced from the inlet opening to afford movement of one of the staples into the passageway, along said passageway toward an eject position at which the end portion of the ram pushes the staple to said outlet opening; and drive means activatable to move said ram from said load to said eject position.

4. A stapler according to claim 3 wherein said track further comprises a second portion disposed with respect to said first portion at an angle of less than 180 degrees measured on the side of said track opposite the projecting legs of said staples, and said first and second track portions are adjacent and are both linear.

5. A stapler according to claim 4 wherein said second track portion is generally parallel to said passageway, and said track includes a third portion that is arcuate about an axis parallel to said surfaces and joins said first and second portions with the staples along said arcuate third portion being disposed with their legs projecting generally normally away from the axis of said arcuate third portion.

6. A stapler according to claim 5 wherein said means for biasing the central portions of said staples along said track comprises a flexible follower plate having a width and thickness of the central portion of a staple to be dispensed, having one end in contact with the central portion of the adjacent staple, and being flexible about an axis transverse of its width to allow it to move around said arcuate third portion and into said first portion to press said staples toward said inlet opening.

7. A surgical stapling apparatus adapted for use with a skin-stapling instrument in applying surgical staples to disunited skin or fascia, each staple including a pair of spaced-apart, parallel legs joined by a crown, the legs and crown of each staple defining the plane of the staple, said apparatus comprising:

a longitudinal staple-driving channel along which the staples are driven one at a time in succession in the distal direction, each staple being oriented in said staple-driving channel so that the plane of the staple is parallel to the longitudinal axis of the staple-driving channel and so that the free ends of the staple legs, remote from the crown, point in the distal direction;

a staple-storing channel for storing a plurality of said staples in a sequential array prior to delivery of said staples one at a time to said staple-driving channel; and spring means acting on the proximal-most staple in said staple-storing channel for constantly urging the staples as a total charge in the distal direction along said staple-storing channel;

said staple-storing channel comprising connecting channel means communicating with a proximal portion of said staple-driving channel for conveying staples one at a time to the proximal portion of said staple-driving channel in response to the urging of said spring means and for orienting the staples as they are thus conveyed so that the plane of each staple exiting from said connecting channel means is parallel to the longitudinal axis of said staple-driving channel with the free ends of the staple legs pointing in the distal direction, the included angle between the axis of said connecting channel means immediately adjacent to said staple-driving channel and the portion of the longitudinal axis of said staple-driving channel along which the staples are driven being substantially less than 90°.

8. A surgical stapling apparatus adapted for use with a skin-stapling instrument in applying surgical staples to disunited skin or fascia, each staple including a pair of spaced-apart, parallel legs joined by a crown, the legs and crown of each staple defining the plane of the staple, said apparatus comprising:

a longitudinal staple-driving channel along which the staples are driven one at a time in succession in the distal direction, each staple being oriented in said staple-driving channel so that the plane of the staple is parallel to the longitudinal axis of the staple-driving channel and so that the free ends of the staple legs, remote from the crown, point in the distal direction;

a longitudinal staple-storing channel for storing a plurality of said staples in a sequential array prior to delivery of said staples one at a time to said staple-driving channel, the longitudinal axis of the staple-storing channel being substantially parallel to and spaced from the longitudinal axis of said staple-driving channel, the staples being oriented in said staple-storing channel so that the planes of the staples are transverse to the longitudinal axis of said staple-storing channel but parallel to one another, adjacent staples in said staple-storing channel being in side-by-side physical contact with one another, the free ends of the legs of all of the staples in said staple-storing channel pointing in a substantially common direction away from the longitudinal axis of the staple-driving channel;

spring means acting on the proximal-most staple in said staple-storing channel for constantly urging the staples as a total charge in the distal direction along said staple-storing channel; and connecting channel means communicating with the distal end of said staple-storing channel and with a proximal portion of said staple-driving channel for conveying staples one at a time from the distal end of said staple-storing channel to the proximal portion of said staple-driving channel in response to the urging of said spring means and for reorienting the staples as they are thus conveyed so that the plane of each staple exiting from said connecting channel means is parallel to the longitudinal axis of said staple-driving channel with the free ends of the staple legs pointing in the distal direction, the included angle between the portion of the longitudinal axis of said connecting channel means immediately adjacent to said staple-driving channel and the portion of the longitudinal axis of said staple-driving channel along which the staples are driven being substantially less than 90°.

9. The apparatus of claim 8, further comprising anvil means transverse to the distal end of said staple-driving channel for contacting a central portion of the crown of a staple driven to the distal end of said staple-driving channel and for providing a structure around which the staple is bent to redirect the free ends of the staple legs toward one another.

10. The apparatus of claim 9, further comprising pusher means reciprocally mounted in said staple-driving channel for pushing a staple, conveyed to said staple-driving channel by said connecting channel means, from the proximal portion of said staple-driving channel to said anvil means and for bending the staple about said anvil means.

11. A surgical stapling apparatus adapted for use with a skin-stapling instrument in applying surgical staples to disunited skin or fascia, each staple being formed of metal wire of circular cross section and including a pair of spaced-apart, parallel legs joined by a crown, the legs and crown of each staple defining the plane of the staple, said apparatus comprising:

a longitudinal staple-driving channel along which the staples are driven one at a time in succession in the distal direction, each staple being oriented in said staple-driving channel so that the plane of the staple is parallel to the longitudinal axis of the staple-driving channel and so that the free ends of the staple legs, remote from the crown, point in the distal direction;

a longitudinal staple-storing channel for storing a plurality of said staples in a sequential array prior to delivery of said staples one at a time to said staple-driving channel, the longitudinal axis of the staple-storing channel being substantially parallel to and spaced from the longitudinal axis of said staple-driving channel, the staples being oriented in said staple-driving channel, the staples being oriented in said staple-storing channel so that the planes of the staples are transverse to the longitudinal axis of said staple-storing channel but parallel to one another, adjacent staples in said staple-storing channel being in side-by-side physical contact with one another, the free ends of the legs of all of the staples in said staple-storing channel pointing in a substantially common direction away from the longitudinal axis of the staple-driving channel;

spring means acting on the proximal-most staple in said staple-storing channel for constantly urging the staples as a total charge in the distal direction along said staple-storing channel; and connecting channel means communicating with the distal end of said staple-storing channel and with a proximal portion of said staple-driving channel for conveying staples one at a time from the distal end of said staple-storing channel to the proximal portion of said staple-driving channel in response to the urging of said spring means, said connecting channel means including an initial longitudinally curved portion for guiding the crowns of a succession of staples exiting from said staple-storing channel in a direction toward the longitudinal axis of said staple-driving channel so that the crown of each succeeding staple contacts the legs of the preceding staple and thereby tends to rotate said preceding staple about the axis defined by the crown of staple in the direction which tends to point the legs of said preceding staple in the distal direction, said curved portion extending a sufficient distance so that the plane of the distal-most staple in said curved portion is rotated substantially parallel to the longitudinal axis of said staple-driving channel, said connecting channel means further including a longitudinally straight portion for conveying the staples from said curved portion to the proximal portion of said staple-driving channel, the included angle between the longitudinal axis of said straight portion and the longitudinal axis of said staple-driving channel being substantially less than 90°.

12. The apparatus of claim 11, wherein the legs of the staple in the proximal portion of said staple-driving channel are supported parallel to the longitudinal axis of said staple-driving channel by the legs of the adjacent staple that is in said connecting channel means.

13. The apparatus of claim 11, further comprising anvil means transverse to the distal end of said staple-driving channel for contacting a central portion of the crown of a staple driven to the distal end of said staple-driving channel and for providing a structure around which the staple is bent to redirect the free ends of the staple legs toward one another.

14. The apparatus of claim 13, further comprising pusher means reciprocally mounted in said staple-driving channel for pushing a staple, conveyed to said staple-driving channel by said connecting channel means, from the proximal portion of said staple-driving channel to said anvil means and for bending the staple about said anvil means.

15. A surgical stapling apparatus adapted for use with a skin-stapling instrument in applying surgical staples to disunited skin or fascia, each staple including a pair of spaced-apart, parallel legs joined by a crown, the legs and crown of each staple defining the plane of the staple, said apparatus comprising:

a longitudinal staple-driving channel along which the staples are driven one at a time in succession in the distal direction, each staple being oriented in said staple-driving channel so that the plane of the staple is parallel to the longitudinal axis of the staple-driving channel and so that the free ends of the staple legs, remote from the crown, point in the distal direction;

a longitudinal staple-storing channel for storing a plurality of said staples in a sequential array prior to delivery of said staples one at a time to said staple-driving channel, the longitudinal axis of the staple-storing channel being spaced from the longitudinal axis of said staple-driving channel, the staples being oriented in said staple-storing channel so that the planes of the staples are transverse to the longitudinal axis of said staple-storing channel but parallel to one another, adjacent staples in said staple-storing channel being in side-by-side physical contact with one another, the free ends of the legs of all of the staples in said staple-storing channel pointing in a substantially common direction away from the longitudinal axis of the staple-storing channel;

spring means acting on the proximal-most staple in said staple-storing channel for constantly urging the staples as a total charge in the distal direction along said staple-storing channel; and connecting channel means communicating with the distal end of said staple-storing channel and with a proximal portion of said staple-driving channel for conveying staples one at a time from the distal end of said staple-storing channel to the proximal portion of said staple-driving channel in response to the urging of said spring means and for reorienting the staples as they are thus conveyed so that the plane of each staple exiting from said connecting channel means is parallel to the longitudinal axis of said staple-driving channel with the free ends of the staple legs pointing in the distal direction, the included angle between the portion of the longitudinal axis of said connecting channel means immediately adjacent to said staple-driving channel and the portion of the longitudinal axis of said staple-driving channel along which the staples are driven being substantially less than 90°.

* * * * *